United States Patent
Humayun

(10) Patent No.: US 10,966,738 B2
(45) Date of Patent: Apr. 6, 2021

(54) OCULAR ULTRASOUND PROBE

(71) Applicant: DOHENY EYE INSTITUTE, Los Angeles, CA (US)

(72) Inventor: Mark S. Humayun, Glendale, CA (US)

(73) Assignee: DOHENY EYE INSTITUTE, Los Angeles, CA (US)

( * ) Notice: Subject to any disclaimer, the term of this patent is extended or adjusted under 35 U.S.C. 154(b) by 179 days.

(21) Appl. No.: 15/651,865

(22) Filed: Jul. 17, 2017

(65) Prior Publication Data

US 2018/0185043 A1    Jul. 5, 2018

Related U.S. Application Data

(63) Continuation of application No. 15/378,028, filed on Dec. 13, 2016, now Pat. No. 10,743,896, which is a continuation of application No. 14/272,161, filed on May 17, 2014, now abandoned, which is a continuation of application No. 13/476,984, filed on May 21, 2012, now abandoned.

(60) Provisional application No. 61/577,525, filed on Dec. 19, 2011, provisional application No. 61/488,505, filed on May 20, 2011.

(51) Int. Cl.
| | |
|---|---|
| *A61B 17/225* | (2006.01) |
| *A61N 7/00* | (2006.01) |
| *A61B 8/10* | (2006.01) |
| *A61B 8/08* | (2006.01) |
| *A61F 9/007* | (2006.01) |
| *A61B 8/00* | (2006.01) |
| *A61B 17/22* | (2006.01) |

(52) U.S. Cl.
CPC .............. *A61B 17/225* (2013.01); *A61B 8/08* (2013.01); *A61B 8/10* (2013.01); *A61F 9/00745* (2013.01); *A61N 7/00* (2013.01); *A61B 8/4444* (2013.01); *A61B 8/4483* (2013.01); *A61B 17/2202* (2013.01); *A61N 2007/0039* (2013.01)

(58) Field of Classification Search
CPC ..... A61B 17/225; A61B 8/10; A61F 9/00745; A61N 2007/0039
See application file for complete search history.

(56) References Cited

U.S. PATENT DOCUMENTS

| | | | | |
|---|---|---|---|---|
| 5,179,953 | A * | 1/1993 | Kursar | A61B 3/16 600/399 |
| 6,994,672 | B2 * | 2/2006 | Fleischman | A61B 3/16 600/405 |
| 8,353,595 | B2 * | 1/2013 | Mann | A61B 3/1208 351/206 |
| 2007/0171368 | A1 * | 7/2007 | Smith | A61B 3/14 351/206 |
| 2008/0177220 | A1 * | 7/2008 | Lindgren | A61F 9/0008 604/22 |
| 2009/0030323 | A1 * | 1/2009 | Fawzi | A61B 8/10 600/458 |

(Continued)

*Primary Examiner* — Jason M Ip
(74) *Attorney, Agent, or Firm* — Yakov Sidorin; Quarles & Brady LLP

(57) ABSTRACT

Devices, systems and methods for ocular ultrasound are provided having therapeutic and/or diagnostic applications. In one aspect, an ocular probe is disclosed that is uniquely configured for use in the eye on the basis of shape and frequency. The ocular probe may be multi-functional, providing sensor, optical or other functionality in additional to ultrasound energy.

14 Claims, 12 Drawing Sheets

Pre-retinal pO2 measurements near one of the occluded vessels in rabbit over the 45 minutes of therapeutic US application.

(56) References Cited

U.S. PATENT DOCUMENTS

| | | | | |
|---|---|---|---|---|
| 2010/0226971 A1* | 9/2010 | Chau | ................... | A61F 9/0017 424/450 |
| 2010/0292763 A1* | 11/2010 | Brinkmann | ............. | A61F 9/008 607/89 |
| 2010/0318034 A1* | 12/2010 | Goncalves | ............ | A61F 9/0017 604/174 |

* cited by examiner

Collapse of Retinal Veins and Sclerosis

Doppler Imaging

Doppler imaging of retina in the US+MB group shows no recordable retinal venous blood flow as measured from the retinal surface (A), while after MB-enhanced US thrombolysis retinal venous blood flow in the treated vein is restored and the calculated average blood velocity is 1.0 cm/s (B).

Mean retinal venous blood velocity as measured before and after the process. The US+MB group showed statistically significant improvement of blood flow.
* refers to $P<0.05$ with statistical significance

OCULAR ULTRASOUND PROBE

CROSS-REFERENCE TO RELATED APPLICATIONS

This application claims priority to U.S. Provisional Application No. 61/488,505 filed May 20, 2011, titled "Ocular Ultrasound Probe" and U.S. Provisional Application No. 61/577,525, filed Dec. 19, 2011, titled "Ocular Ultrasound Probe," both of which are incorporated herein by reference.

FIELD OF THE INVENTION

The present invention relates to devices, systems and methods for ocular ultrasound having therapeutic and/or diagnostic applications.

BACKGROUND OF THE INVENTION

Proper functioning of the eye requires nourishment from the vascular system. A disruption in blood flow can lead to a disruption in vision or even blindness. A variety of diseases and disorders can cause disruption in ocular blood flow.

Retinal vein occlusion (RVO) is a condition in which a blood clot slows or stops circulation in a vein within the retinal tissue. There are two primary types of RVO. Central retinal vein occlusion (CRVO) involves a blockage of the main vein of the retina. Branch retinal vein occlusion (BRVO) involves a blockage of the tributary vein(s) of the retina. RVO is the second most common retinal vascular disease and is a significant cause of blindness worldwide. In the U.S. alone, 150,000 new cases of RVO occur each year.

Various pharmacological and non-pharmacological treatments for RVO have been explored. Pharmacological treatments include systemic/intravitreal thrombolytics, intravitreal triamcinolone (SCORE: Standard Care Vs. Corticosteroid for Retinal Vein Occlusion; Ozurdex, Allergan), and intravitreal anti-VEGF (bevacizumab, ranibizumab, pegaptanib). Non-pharmacological treatments for BRVO include limited sheath manipulation, macular laser and sheathotomy. Non-pharmacological treatments for CRVO include laser/surgical chorioretinal anastomosis, posterior scleral ring sheathotomy, radial optic neurotomy and retinal vein cannulation. The surgical approaches to RVO treatment are technically challenging, but when successful, produce significant results.

U.S. Patent Application Publication No. 2009/0030323 to Fawzi et al., titled "Ultrasound and Microbubbles in Ocular Diagnostics and Therapies" described methods, systems, and techniques for applying contrast-enhanced ultrasound to locate areas of blockage within retinal vessels and to break up clots that are causing damage.

There remains a need for improved treatments for diseases and disorders caused by disruption in ocular blood flow, including RVO.

SUMMARY OF THE INVENTION

Disclosed herein are devices, systems and methods for ocular ultrasound having therapeutic and/or diagnostic applications. In one aspect, the present invention is an ocular ultrasound probe which may be configured for extraocular or intraocular use as described herein.

In a first embodiment, the present invention is an ocular ultrasound probe comprising a housing and a transducer element contained within the housing, wherein the transducer element provides a source of ultrasound at a frequency of less than about 10 MHz. In a particular embodiment, the ultrasound frequency is less than about 5 MHz.

In a second embodiment, the present invention is an ocular ultrasound probe comprising a housing and a transducer element contained within the housing, wherein the ocular ultrasound probe is configured to permit simultaneous application of ultrasound energy and viewing of the site to which the ultrasound energy is applied.

In a third embodiment, the present invention is an ocular ultrasound probe that is self-retaining or primarily self-retaining during use, i.e., application of ultrasound energy. In a particular embodiment, the self-retaining ocular ultrasound probe further comprises a securing means. In a specific embodiment, the securing means is an adhesive or strap.

In a fourth embodiment, the present invention is an ocular ultrasound probe configured to permit application of ultrasound energy to the eye while advantageously limiting ultrasound energy delivery to the crystalline lens.

The configuration of the ocular ultrasound probe may vary according to conditions of use. In one embodiment, the present invention is an ocular ultrasound probe comprising a housing or probe head in the shape of a disc, a half-circle, a crescent, a wedge or a ring. In a particular embodiment, the ocular probe is configured for use with an ultrasound bath.

The ocular ultrasound probe may optionally further comprise a sensor to permit the user to determine if the probe is in contact with the patient's eye. The sensor may be any suitable sensor known for use with determining contact with another surface. In one embodiment, the sensor may sense or measure pressure or resistance at the point of contact with the patient. In a particular embodiment, the sensor means is a mechanical or electrical spring.

The ocular ultrasound probe of the present invention may optionally further comprise an optical component. In one embodiment, the optical component is an imaging component. In another embodiment, the optical component is a laser.

The ocular ultrasound probe may optionally further comprise an RFID component, e.g., an RFID tag or reader.

In a fifth aspect, the present invention is a system for delivering ultrasound energy to the eye, which system includes an ocular ultrasound probe and a processor.

In a sixth aspect, the present invention is a method of treating a disease or disorder of ocular blood flow comprising supplying microbubbles to a blockage within a retinal vessel and applying ultrasound energy to the eye using the ocular ultrasound probe of the present invention in order to reduce or eliminate the blockage.

In one embodiment, the disease or disorder is retinal vein occlusion.

Optionally, the method further comprises viewing the blockage prior to, during or after the application or microbubbles or ultrasound energy.

Optionally, the method further comprises administering one or more additional treatments to the eye.

BRIEF DESCRIPTION OF THE DRAWINGS

Aspects of the disclosure may be more fully understood from the following description when read together with the accompanying drawings, which are to be regarded as illustrative in nature, not as limiting. The drawings are not necessarily to scale, emphasis instead being placed on the principles of the disclosure.

Figure 1:
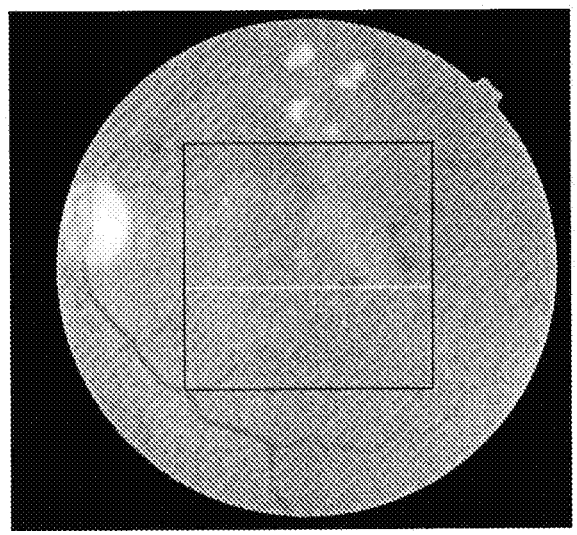
FIG. 1 shows the collapse of retinal veins and sclerosis.
Figure 2:
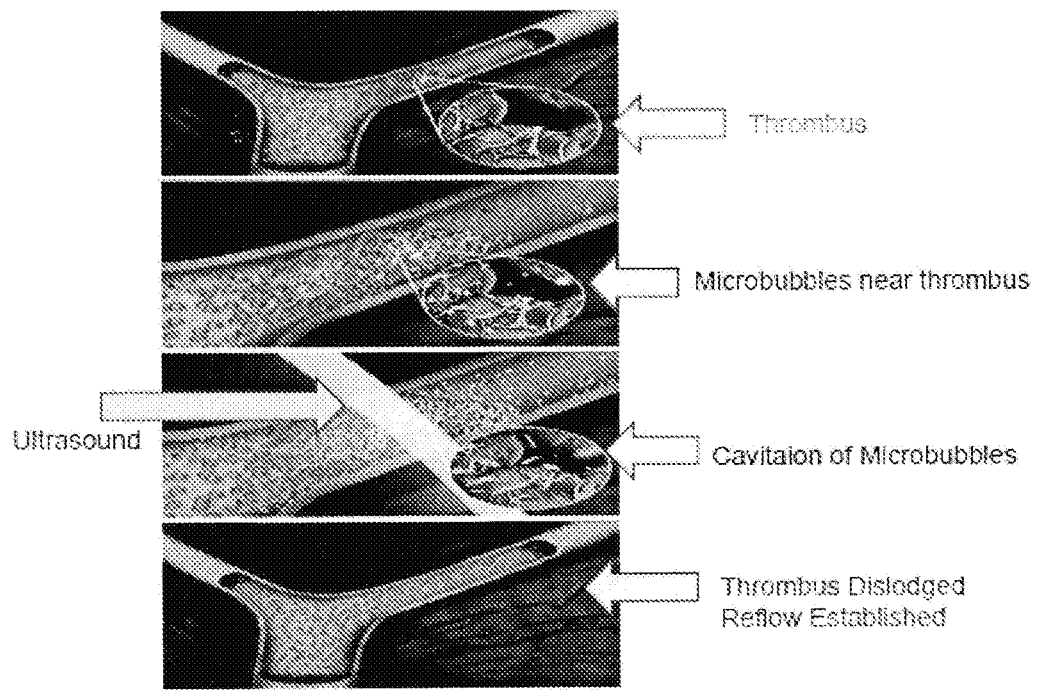
FIG. 2 shows the cavitation of microbubbles using ultrasound to dislodge a thrombus. (Source: Cerevast Therapeutics, Inc.)
Figure 3:
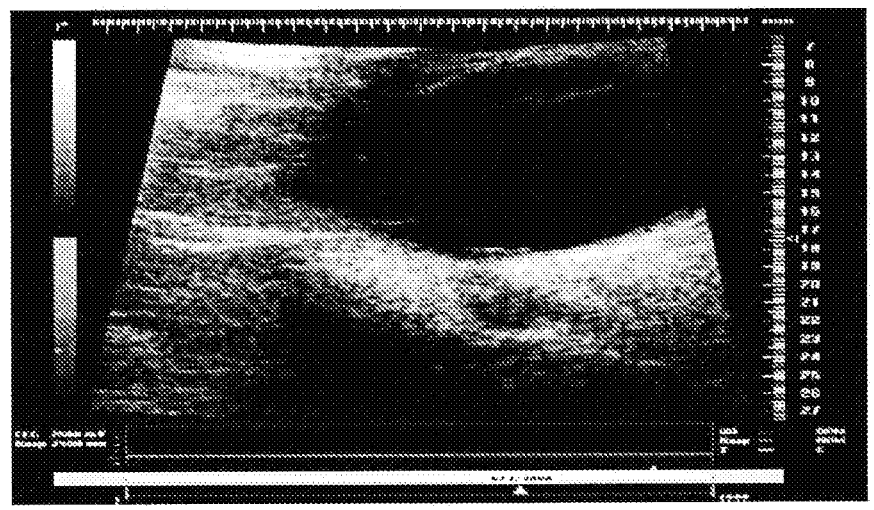
FIG. 3 shows an ultrasound image of microbubble flow in retinal vessels.
Figure 4:
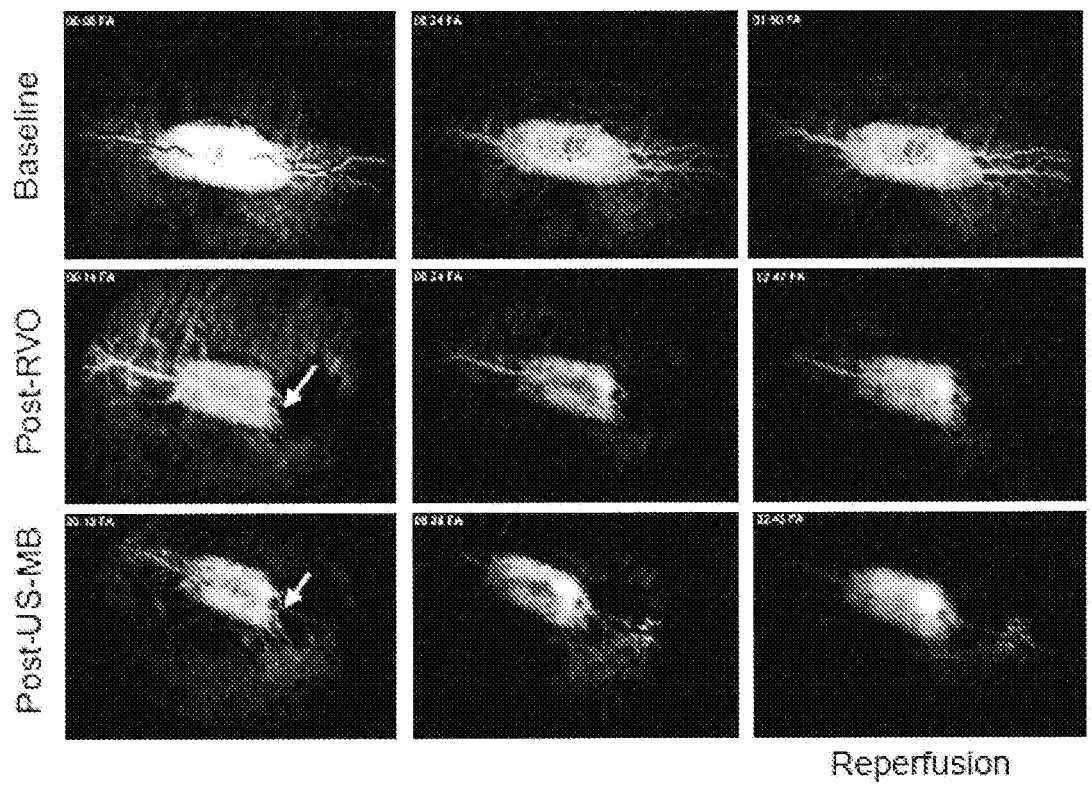
FIG. 4 shows images from a flourescein angiogram in rabbit showing normal perfusion of the retinal vessels (top row), photothrombosis (middle row) and reperfusion after sonolysis treatment (bottom row).
Figure 5:
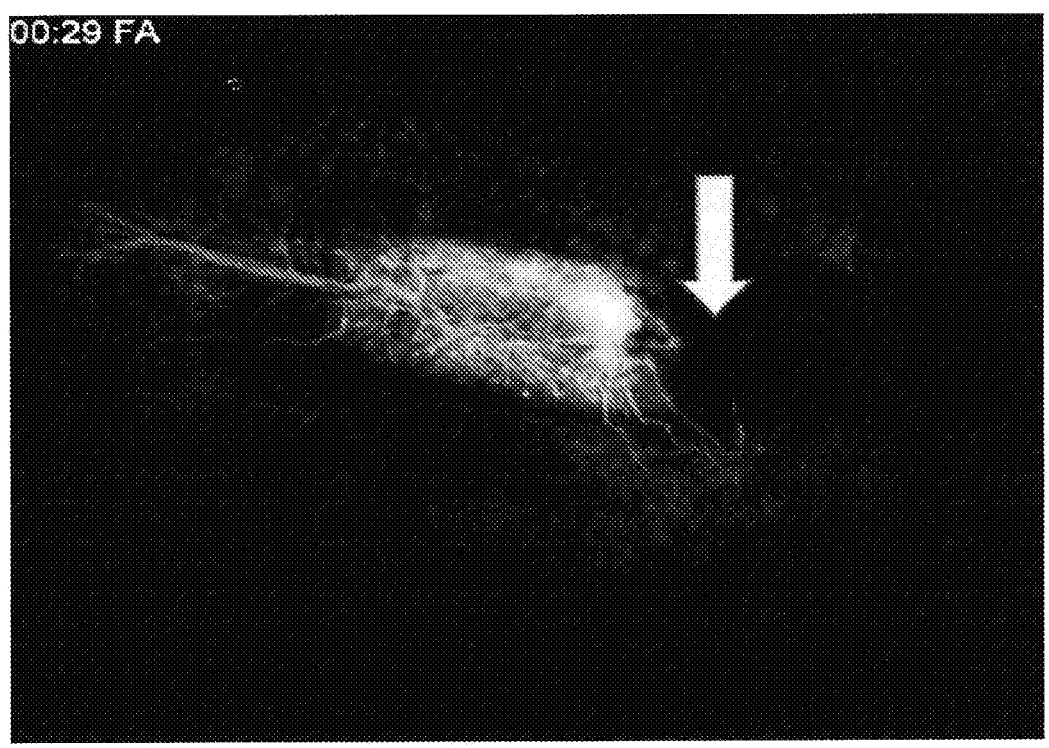
FIG. 5 shows an angiography of a retinal vessel treated with microbubble-assisted ultrasound.
Figure 6:
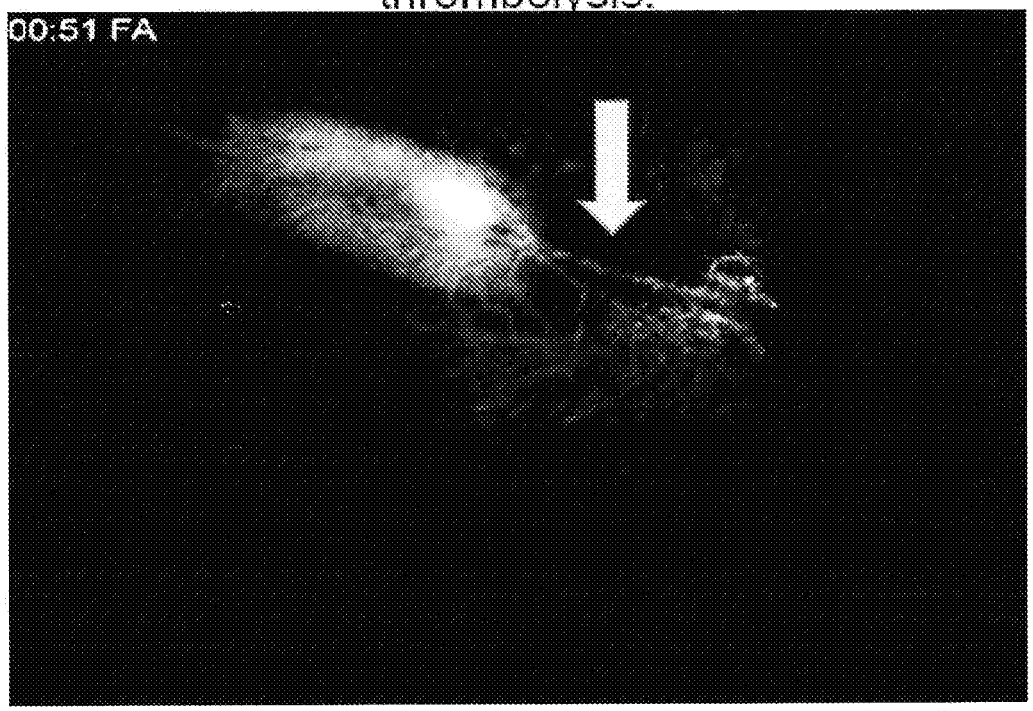
FIG. 6 shows an angiography of a retinal vessel treated with microbubble-assisted ultrasound.
Figure 7:
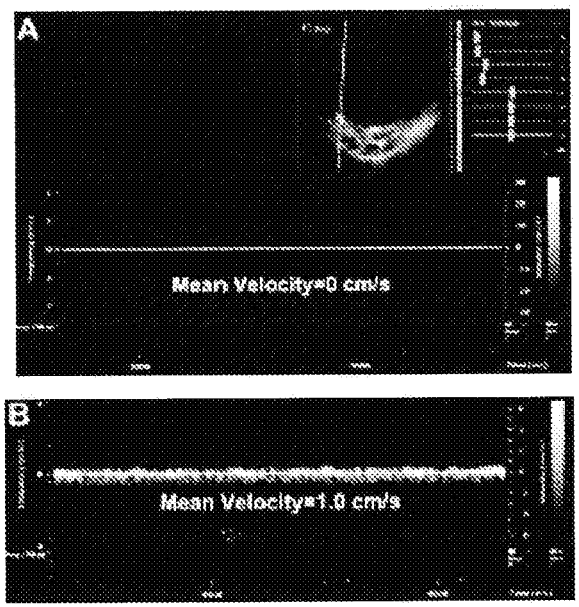
FIG. 7 shows a Doppler image of retina.
Figure 8:
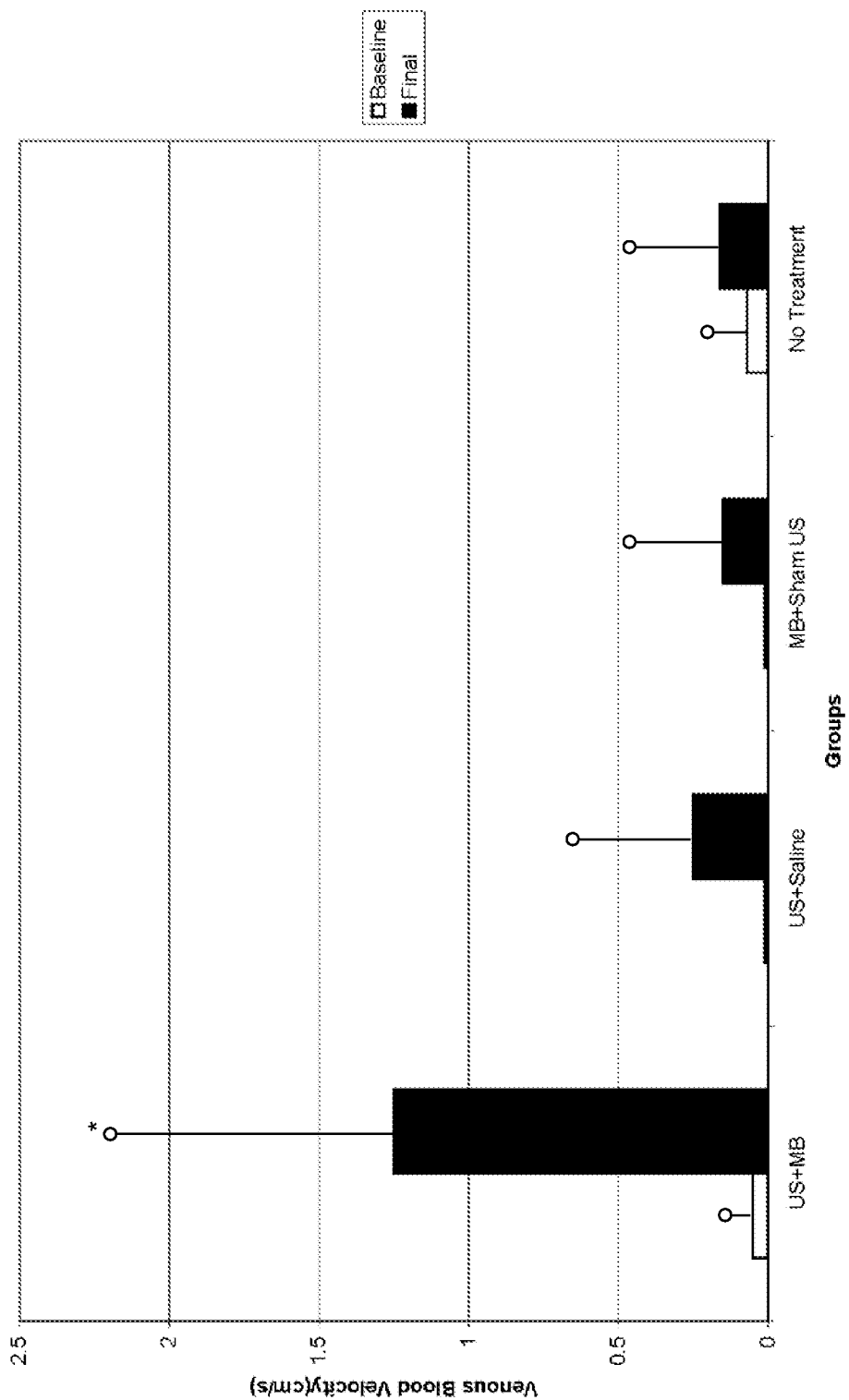
FIG. 8 is a chart depicting the mean venous blood velocity.
Figure 9:
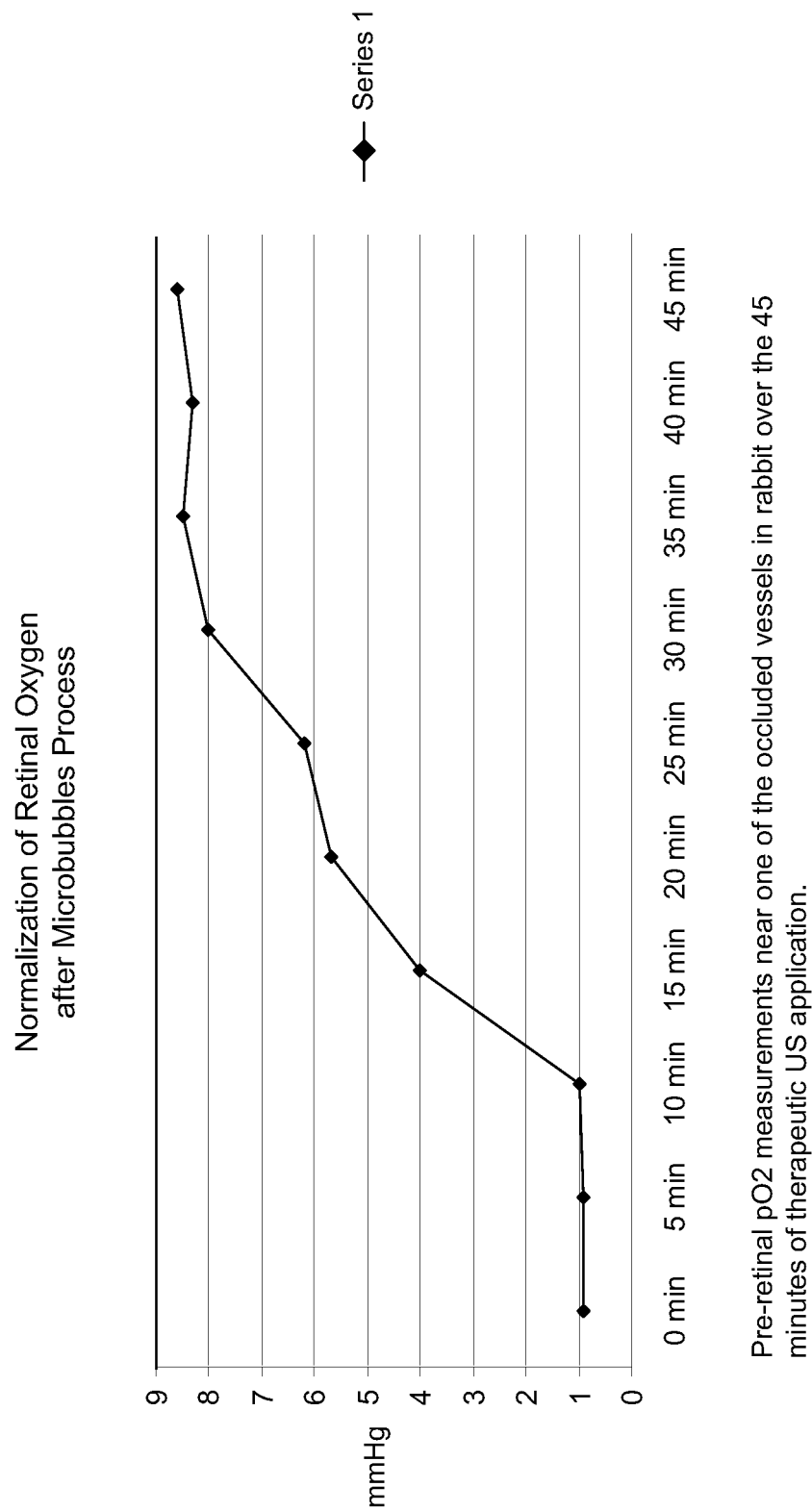
FIG. 9 is a chart depicting the normalization of retinal oxygen after treatment with microbubble-assisted ultrasound.
Figure 10:
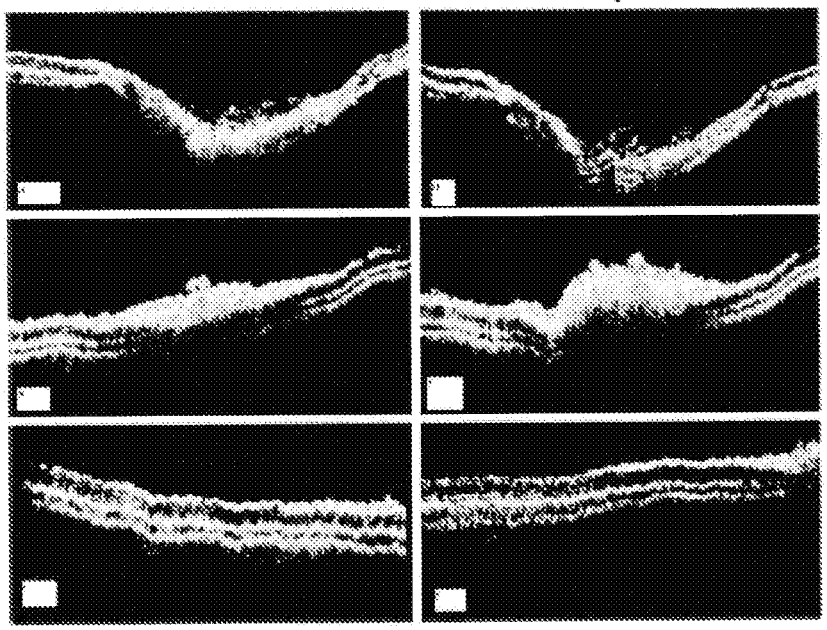
FIG. 10 shows an optical coherence tomography image after treatment with microbubble-assisted ultrasound.
Figure 11:
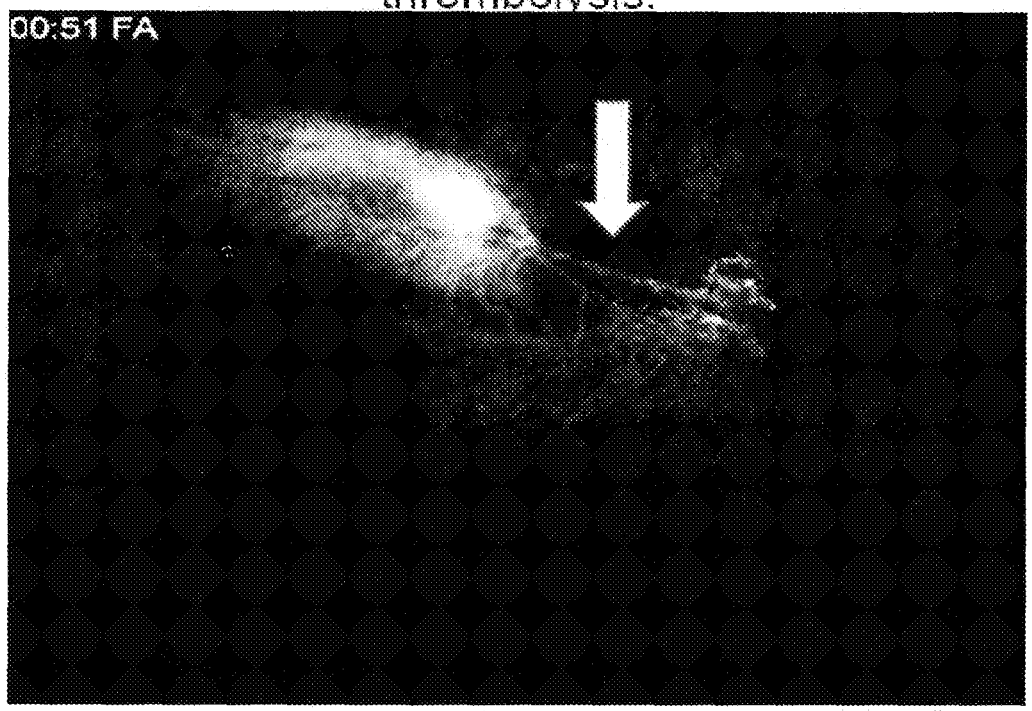
FIG. 11 shows an angiography of a retinal vessel treated with microbubble-assisted ultrasound.

While certain embodiments are depicted in the drawings, one skilled in the art will appreciate that the embodiments depicted are illustrative and that variation of those shown, as well as other embodiments described herein, may be envisioned and practiced within the scope of the present disclosure.

DETAILED DESCRIPTION

Disclosed herein are devices, systems and methods for ocular ultrasound having therapeutic and diagnostic applications.

The Ultrasound Probe

An ultrasound probe configured for ocular use is provided herein. The ocular ultrasound may be an extraocular ultrasound probe or an intraocular ultrasound probe, in each instance comprising a housing and a transducer element contained within the housing.

The transducer element provides the ultrasound component of the probe. The transducer is typically a piezoelectric material or single crystal material which converts electrical energy to ultrasonic energy and ultrasonic energy to electrical energy. The piezoelectric material may be a ceramic, a polymer or a composite material. In a specific embodiment, the transducer element is lead zirconate titanate (PZT).

Transducers for use in the ocular ultrasound probe of the present invention may vary in configuration, including shape, size and/or orientation within the probe housing. PZT transducers, in particular, are desirable based on their ability to be shaped. In one embodiment of the present invention, the shape of the transducer element varies with the shape of the housing. The configuration of the transducer may also vary based on the shape of the ultrasound probe and can be linear, horizontal or vertical.

The ocular probe may contain a single transducer element or multiple transducer elements. Where multiple transducers are utilized within a single probe, the transducers may be spaced regularly or irregularly within the casing. In a particular embodiment, multiple transducers are configured in a linear array.

The thickness of the active element determines the frequency of the transducer, i.e., the number of wave cycles completed in one second, which is typically expressed in Kilohertz (KHz) or Megahertz (MHz). Generally, thin materials have high frequencies while thick materials have low frequencies. Low frequencies are associated with longer wavelengths and generally penetrate deeper in materials. In a particular embodiment, the ocular ultrasound probe of the present invention has a PZT transducer element with a thickness of less than about 20 μm, less than about 15 μm, less than about 10 μm or less than about 5 μm.

In one embodiment, the ocular ultrasound probe of the present invention generates frequencies in the range of from about 1 to about 20 MHz. In a particular embodiment, the ocular ultrasound probe generates frequencies of from about 1 to about 10 MHz. In another particular embodiment, the ocular ultrasound probe generates frequencies of less than about 9, about 8, about 7, about 6, about 5, about 4, about 3, about 2 or about 1 MHZ. In a specific embodiment, the ocular ultrasound probe generates a frequency of less than about 5 MHz. In a particular embodiment, the frequency is less than about 10 MHz and the mechanical index (MI) is below about 0.5.

The ultrasound may be applied generally in a focused or directed manner, where focus refers to the convergence of the mechanical waves on a specific point. The intensity, duration and resonant frequency may be altered according to the particular result desired, for example, diagnostic imaging versus therapeutic use.

The configuration of the ocular probe is dictated by the conditions of use, where configuration variously refers to the shape of the housing, the shape of the transducer, any additional components contained within the housing as well as their orientation, and the external connectivity of the housing to one or more additional components within an ultrasound system.

The shape of the housing may vary. In an exemplary embodiment, the housing has a generally elongated shape having a proximal end and a distal end. In this elongated embodiment, the transducer is generally disposed at the distal end of the probe (i.e., closest to the patient's eye), referred to as a probe head. The probe head is configured to direct ultrasound energy from the transducer to a target location on the patient's body, i.e., the eye. The head portion may be a disk or round shape, a half-circle shape, a crescent shape, a triangle/wedge shape, or a ring/torus shape. A handle/grip portion may be located at the proximal end of the housing, structured to enable a user to grasp the casing and position the ultrasound probe adjacent to the treatment site. The handle/grip portion can include electrical switches which changes the parameters for operating the probe including turning it on and off. In non-wireless embodiments, a cord for transferring data and power typically extends from the proximal end of the ultrasound probe.

In another embodiment, the ocular probe is not elongated but relatively flat. The term flat or relatively flat is used to describe an ultrasound probe having a top surface, a bottom surface and a sidewall, wherein the bottom and top surfaces have a width greater than the height of the sidewalls. The bottom surface refers to the surface in closest proximity to the patient during application of ultrasound, i.e., from which the ultrasound energy is transmitted upon generation by transducer element contained within the housing. According to this embodiment, the flat or relatively flat probe housing may be in the shape of a disk or round shape, a half-circle shape, a crescent shape, a triangle/wedge shape, or a ring/torus shape.

Figure 12A:
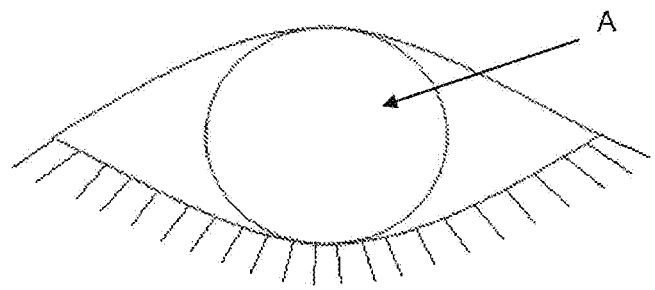
FIG. 12A is an illustration of an exemplary disc-shaped extraocular ultrasound probe (A) shown placed on a closed eyelid.

In a particular embodiment, the ocular probe is an extraocular probe configured for positioning on the external surface of the patient's body, for example on the eyebrow or closed eyelid of the patient to be treated. The probe may be elongated or flat. Where the probe is elongated, the probe head is configured for positioning on the external body surface. When the probe is flat, the housing itself is configured for positioning on the external surface. FIG. 12(A) shows a disc-shaped ultrasound probe placed on a closed eyelid of a patient.

In another embodiment, the ultrasound probe is configured for intraocular use, i.e., for use within the eye. When the use is internal or intraocular, the shape of the ultrasound probe (or the bath used in combination with the probe, as applicable) may be dictated by the shape/contour of the eye surface or eye socket. When the probe housing is elongated, the shape of the probe head is dictated by the eye surface or socket. When the probe is flat or relatively flat, the shape of the housing is dictated by the eye surface or socket. An exemplary ultrasound probe can have a semi-spherical shape similar to a contact lens. The exemplary ultrasound probe can cover a portion of the eye surface and can be placed in the same/similar location as contact lens would be placed. It is also contemplated that the ultrasound probe can be moved along the eye surface to various locations. In another particular embodiment, the ultrasound probe is configured for use in the eye socket. For example, the ultrasound probe can cover most or all of the eye surface. An exemplary ultrasound probe includes an outer ring that fits snuggly to the patient's eyelids.

In one embodiment, the ocular ultrasound probe advantageously permit the user to simultaneously apply ultrasound energy and view the same, i.e., view the target site to which ultrasound energy is being directed. In an exemplary embodiment, the ultrasound probe is configured to permit the ultrasound operator or user to view the eye during ultrasound application or while the ultrasound probe is in position for ultrasound application using an microscope or other viewing instrument. In a particular embodiment, the ultrasound probe has a half circle, torus, crescent, or wedge shape that permits the user to look into the patient's eye during the ultrasound treatment using a microscope or other viewing instrument.

In another embodiment, the ocular ultrasound probe advantageously permits ultrasound energy to be delivered to the eye while limiting ultrasound energy delivery to the crystalline lens. That is, the shape of the probe is such that ultrasound energy can be delivered to the target site within the eye while avoiding the crystalline lens. For example, the torus shaped probe can be placed in the patient's eye such that the open center portion of the torus encircles the natural lens of the patient's eye, thereby preventing exposure to ultrasound energy.

According to one aspect of the invention, the ocular ultrasound probe is self-retaining or primarily self-retaining, where self-retaining refers to the ability to remain fixed in position at the site of use while ultrasound is applied without the need for the user to hold the probe in place, either at all or for extended periods of time otherwise required. This self-retaining probe can be extraocular or intraocular, where the unaided or relatively unaided retention is possible due to the configuration of the housing and/or the use of one or more securing means.

In one embodiment, the ultrasound probe is advantageously configured to limit or obviate the need for the user or operator to hold the ultrasound probe as the method is performed. The need to hold the probe during use is either completely eliminated or reduced to some degree over the duration required by a standard probe (e.g., less than about 60 minutes, about 45 minutes, about 30 minutes, about 15 minutes, about 10 minutes or about 5 minutes). For example, an exemplary ultrasound probe can be positioned proximate a target, i.e., the patient's eye, using securing means or attachment device. For example, the attachment device may retain the ultrasound probe such that neither the user nor the patient are required to position or hold the ultrasound probe in place during application. In a particular embodiment, the securing means is an adhesive applied to the surface of the probe and/or the patient. The adhesive may be, for example, a single or multiple layer adhesive. The adhesive may be capable of single use/attachment or it may be re-sealable upon relocation of the ultrasound probe. In an alternate embodiment, the attachment device can include an apparatus or device worn by the patient to secure the ultrasound probe in place physically against the target location. An exemplary attachment device can include a strap or headpiece for securing the ultrasound probe in place at the patient's eye. For example, the attachment device can be configured similar to an eye patch ('pirate patch") attached around the patient's head by an elastic or cloth band, or as an adhesive bandage.

Exemplary self-retaining ultrasound probes can be a donut shape, a disc shape, a half-circle shape, a crescent shape, a wedge shape or a ring/torus shape.

In one embodiment, the present invention is a self-retaining extraocular probe where the ability to self-retain is provided by the configuration or shape of the probe housing or the probe further comprises one or more securing means. The securing means may be any suitable means including but not limited to an adhesive (to be applied to the probe or the patient or both) or a strap. In a particular embodiment, the extraocular probe is flat and fits within a pirate patch-type securing means which positions the probe on the eyebrow or closed eyelid of the patient when worn by the patient.

In an exemplary embodiment, the self-retaining ultrasound probe is an intraocular probe that may be contoured, similar to the cornea, to sit on the surface of the patient's eye and fit in or adjacent to the patient's eyelids. An exemplary self-retaining intraocular ultrasound probe can have a semi-spherical shape similar to a contact lens. The exemplary ultrasound probe can cover a portion of the eye surface and can be placed in the same/similar location as contact lens would be placed. It is also contemplated that the ultrasound probe can be moved along the eye surface to various locations. In another particular embodiment, the ultrasound probe is configured for use in the eye socket. For example, the ultrasound probe can cover most or all of the eye surface. An exemplary ultrasound probe includes an outer ring that fits snuggly to the patient's eyelids. In one embodiment, the self-retaining intraocular ultrasound probe would be operational when the patient's eyelid is closed.

Figure 12B:
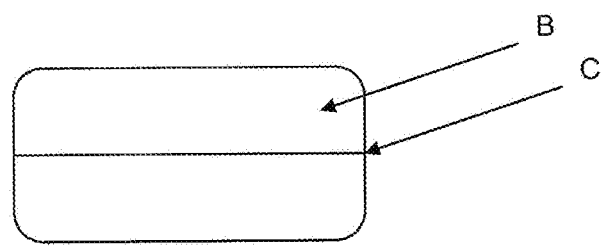
FIG. 12B is an illustration of an exemplary ocular ultrasound probe and spring sensor, according to certain exemplary embodiments.
Figure 12C:
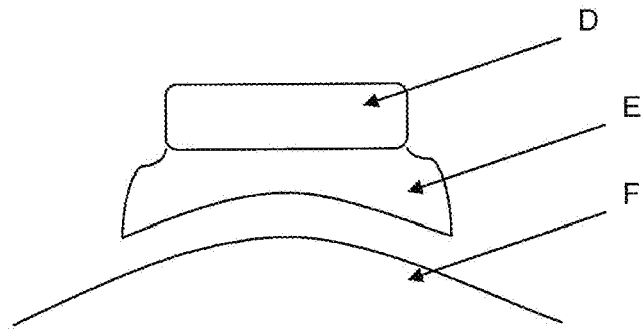
FIG. 12C is an illustration of an exemplary ultrasound probe, bath, and human subject, according to certain exemplary embodiments.

The ultrasound probe may be used alone or in combination with a bath, such as a water bath or gel bath. The ultrasound probe may be attached to the bath or rest within the bath, and in either case, may be configured particularly for this method. Use of the bath permits the sonographer to focus the ultrasound on the front of the patient's eye. For example, in a particular embodiment when the ultrasound probe is functioning at a low frequency, such as 1 MHz, it may be difficult to focus on the physical structures in the front of the patient's eye, e.g., the trabecular meshwork (tissue in the eye located around the base of the cornea providing fluid drain for the eye). By using a bath, the distance between the ultrasound probe and the target tissue/structure is increased, thereby permitting focusing of the ultrasound at the target tissue/structure. In a particular embodiment, an exemplary ultrasound probe can be used in conjunction with a bath for anterior ocular structures. In a particular embodiment, an exemplary ultrasound probe can be used in conjunction with a bath for the treatment of glaucoma. An exemplary bath can be configured to be placed in the eye socket similar to a contact lens. Another exemplary embodiment, illustrated in FIG. 12C shows an ultrasound probe (D) can be attached to the bath (E), which is then placed in contact with the eye (F). The ultrasound probe may be attached to the bath (e.g., by pre-fabrication) or simply rest within it.

In an exemplary embodiment, the ultrasound probe can include both an ultrasound component (e.g., transducer) and an optical component. The optical component can be an imaging component or a treatment component. The optical component can include, for example, a light source. This light source may be any known to one of skill in the art, including, but not limited to light optical fibers, light emitting diodes (LED), xenon arc lamps, halogen bulbs, lasers and the like. In a particular embodiment, the ultrasound probe has a built-in light optical fiber for emitting light onto the patient's body. In one embodiment, the light source emits energy with wavelengths in the visible light spectrum. In other embodiments, the light source emits energy with wavelengths outside the visible light spectrum. An exemplary ultrasound probe may have separate compartments or housings for the transducer and optical components. In an alternative embodiment, the transducer and the optical components are housed in a single unit. In one embodiment, the ultrasound probe is designed to allow simultaneous visualization of human body parts during ultrasound application. In one embodiment, the ultrasound probe combines ultrasound and optical viewing to allow the ultrasound to be used with a microscope and/or digital viewing system. In one embodiment, the ultrasound is configured for use in optical coherence tomography (OCT).

In an exemplary embodiment, the ultrasound probe is configured for use in non-ocular applications. For example, the probe may be used on other regions of the body where ultrasound or ultrasound and imaging capabilities are desired. In a particular embodiment, as described further herein, the ultrasound probe provides ultrasound energy to diagnose the presence of a blood clot or blockage. In a particular embodiment, as described further herein, the ultrasound probe provides ultrasound energy to activate or create inertial or unstable cavitation in a microbubble contrast agent. In another particular embodiment, the ultrasound probe provides ultrasound energy to activate or create inertial or unstable cavitation in a microbubble contrast agent and optical viewing to permit simultaneous viewing of the effects of sonolysis on retinal blood flow and retinal structures. In one example, ocular blood flow may be monitored and adverse effects, such as bleeding, may be identified using the ultrasound probe described herein. In another particular embodiment, the ultrasound probe provides ultrasound and optical viewing to create inertial or unstable cavitation in a microbubble contrast agent and simultaneous viewing of the effects of sonolysis on phacomemulsification (ultrasound assisted breaking of the crystalline lens). In another particular embodiment, the ultrasound probe provides ultrasound energy to permit activation or create inertial or unstable cavitation of a contrast agent or microbubble containing drug or dye label. In another particular embodiment, the ultrasound probe provides ultrasound energy to permit activation or create inertial or unstable cavitation of a contrast agent or microbubble containing drug or dye label as well as optical viewing to permit, and simultaneous viewing of, the effects of sonolysis on drug and/or dye release in the eye. In another particular embodiment, the ultrasound probe provides ultrasound (and optionally, optical viewing) to create inertial or unstable cavitation in a microbubble contrast/dye agent (for example, protoporphyrin) and, optionally simultaneous application of laser to excite the dye). In one embodiment, the ultrasound probe allows accurate measurement of intraocular lens calculations and the accurate measurement of intraocular structures such as the retina as well as pathological structures such as tumors. In one particular embodiment, the optical measure is interferometry. In one embodiment, the ultrasound probe combines ultrasound and optical measures such as lasers to allow combining ultrasound diagnostics and therapeutics with laser diagnostics and therapeutics.

According to one exemplary embodiment, the present ultrasound probe has a tip/cover surface that is detachable, disposable, and/or sterilizable. The tip/cover surface may be pre-packaged. In one embodiment, the ultrasound probe and/or the detachable tip/covers surface are packaged with tools to attach the tip/cover to the ultrasound probe.

In one embodiment, the ultrasound probe includes a sensor to permit the ultrasound machine or user to determine if the probe is in contact with the eye, for example the eyelid or the eye surface. The sensor may be any suitable sensor, including but not limited to, a device to sense or measure pressure or resistance at probe when in contact with the patient. In a particular embodiment, the sensor includes a mechanical or electrical spring to measure pressure or resistance at the point of contact with the patent. An exemplary sensor includes the mechanical or electrical spring located around the perimeter of the housing at the portion of the ultrasound probe including the transducer. In an exemplary embodiment, the sensor includes a mechanical or electrical spring located within the attachment device. In one embodiment, the spring is a ring-shaped spring that is compressed and either mechanically or electrically confirms contact with the eye, e.g., the eyelid or the eye surface. An exemplary sensor is illustrated in FIG. 12(B) including the ultrasound probe (B) and the spring (C). In an alternate embodiment, the ultrasound probe can include capacitance sensors such that the ultrasound probe or attachment device includes sensors for detecting a change in the electrical field at the surface of the probe or attachment device caused by contact with the patient.

In one embodiment, the device is an ultrasound probe wherein such ultrasound probe is either free standing or connected to additional components to provide an ultrasound system. The additional components may include, for example, an amplifier, a processor, a display device, and a keyboard and/or other input and output devices. In one embodiment, the ultrasound probe is wirelessly connected to an additional component. In a particular embodiment, the ultrasound probe includes a Bluetooth module or other suitable short-range wireless device for wireless communication to the ultrasound machine for power and data.

In another embodiment, the present invention is a system for delivering ultrasound energy to the eye, which system includes an ultrasound probe and a processor. Additional components may include a transducer controller for altering the frequency, amplitude or duration of the pulse emitted from the ultrasound probe), a display, an input function (e.g., a keyboard), an information storage device and/or a printer.

The system or any component of the system, including the ultrasound probe, may optionally use radio frequency identification (RFID) technology. In a specific embodiment, the ultrasound probe may have an RFID reader that can read an RFID tag present, for example, on an ultrasound machine or a vial of medicine. In another embodiment, the ultrasound probe may have an RFID tag and an RFID reader may be present in another component of the ultrasound system, remote from the ultrasound reader. In a particular embodiment, the ultrasound probe is activated when the RFID or other similar marking on the transducer and/or housing is recognized by an ultrasound machine or when the RFID of the transducer and/or housing plus the RFID on any associated other component used with the ultrasound probe (e.g., drug vial, ultrasound gel) are both recognized by the ultrasound machine.

Methods of Use

The devices and systems of the present invention can be used in a variety of therapeutic and diagnostic applications, as would be understood to one of skill in the art. In certain embodiments, the device and method provide dual functionality where that is desired for therapeutic and/or diagnostic applications.

In an exemplary embodiment, the present invention is a method of diagnosing an ocular disease or disorder, such as retinal vein occlusion by applying ultrasound energy to the eye using the ocular ultrasound probe or system disclosed herein.

In another embodiment, the present invention is a method of treating an ocular disease or disorder, such as retinal vein occlusion, using the ocular ultrasound probe of the present invention. In a particular embodiment, the method involves administering a therapeutically effective amount of a microbubble contrast agent to the patient and applying ultrasound energy to the eye using the ultrasound probe or system disclosed herein, wherein the ultrasound energy is applied at a frequency of less than about 10 MHz or less than about 5 MHz. In a specific embodiment, the ultrasound energy is applied at about 10, about 9, about 8, about 7, about 6, about 5, about 4, about 3, about 2 or about 1 MHz with a mechanical index (MI) of about 0.5.

In a particular embodiment, the ultrasound probe can be used to activate or create inertial or unstable cavitation in a microbubble contrast agent and, optionally, to allow simultaneous viewing of the effects of such sonolysis on retinal blood flow and retinal structures. In one example, ocular blood flow may be monitored and adverse effects, such as bleeding, may be identified using the methods described herein.

Microbubbles are tiny, gas-filled lipid, or fat, bubbles that can be injected into the bloodstream, where they remain inactive unless stimulated. Ultrasound energy or waves directed at microbubbles cause the microbubbles to vibrate and return a unique echo within the bloodstream that produces a dramatic distinction, or high "contrast," between blood vessels and surrounding tissue, thus enabling clinicians to visualize areas of restricted blood flow. Specialized Doppler ultrasound, which measures the rate and volume of blood flow, can further pinpoint the extent and severity of blockage caused by blood clots. In one embodiment, visualization is further enhanced utilizing the optical aspects of the probe. In a particular embodiment, the method utilizes microbubbles having from about 1 to about 10 microns in diameter.

Contrast-enhanced ultrasound, further enhanced with the addition of optic visualization, not only allows one to locate areas of blockage within retinal vessels, but also can be used to break up clots that are causing damage. In some instances, the vibration effect of the ultrasound itself may suffice to dislodge clots. In other instances, the microbubbles are ruptured by the sonic energy and the clot is mechanically disrupted. In addition to identifying and treating the damaged area, the ultrasound produces an initial image that may serve as a baseline for monitoring the effect of treatment on the vessel. This initial image may be further enhanced with the use of the optical aspects of the probe.

In one embodiment, the present invention is a method of treating an ocular disease or disorder, such as retinal vein occlusion, in a patient in need thereof, by administering a therapeutically effective amount of a microbubble contrast agent to the patient and applying ultrasound energy to the eye using the ultrasound probe or ultrasound disclosed herein. The microbubbles may be administered to the patient by any suitable method, including, for example, intravenous injection, intraocular injection or extraocular administration. In a particular embodiment, the microbubbles are delivered by intravenous injection into the systemic circulation. In another particular embodiment, the microbubbles are delivered into the retinal blood vessels by way of a catheter. In another particular embodiment, the microbubbles are delivered by intraocular injection. In a still further embodiment, the microbubbles are administered to the patient by placing a drop of fluid or liquid containing the gas microbubbles suspension on the surface of the eye.

The ultrasound energy can be applied generally or in a focused or directed manner. The intensity, duration and resonant frequency may be altered according to the particular result desired, for example, diagnostic imaging versus therapeutic use. In a particular embodiment, the frequency is from about 1 to about 10 MHz and the mechanical index is below about 0.5. In a specific embodiment, the frequency is from about 9, about 8, about 7, about 6, about 5, about 4, about 3, about 2 or about 1 MHz. In a specific embodiment, the frequency is less than about 5 MHz.

After a period ranging from a few minutes to a few hours the eye is inspected using a microscope and then if need be, treatment is continued or discontinued if it has met its end goal. The end goal of the treatment can be establishing reflow in an occluded vessel, or breaking up a lens or lowering intraocular pressure (IOP). At the end of the procedure the ultrasound probe is removed as well as the intravenous injection line.

Optionally, the method of treatment involves viewing the treatment area. The treatment area may be viewed prior to treatment, during treatment (i.e., simultaneously with application of ultrasound energy or other treatments) or after treatment. Viewing the treatment area prior to or during treatment may permit the user to direct the treatment in an optimal manner, while post-treatment viewing may permit the user to determine the effectiveness of the treatment.

In one embodiment, the method involves simultaneous visualization or imaging of human body parts. For example, the user may visualize the patient's body parts using ultrasound images while simultaneously visualizing portions of the patient's body using the disclosed optical element.

In one embodiment, the ultrasound probe is centered on the body part during surgery or clinical examination (e.g., torus/ring-shaped probe or contact lens-shaped probe placed on the eye during surgery or clinical examinations).

Optionally, the method of treatment involves one or more additional therapeutic steps. In a particular embodiment, the method also involves applying laser energy to the eye using the ultrasound probe or system disclosed herein. In a particular embodiment, the method involves applying laser energy to the eye to provide one or more of photo acoustics, photo excitation or photocoagulation.

In one embodiment, the method combines diagnosis and treatment. In a particular embodiment, the present invention is a method of diagnosing an ocular disease or disorder, such as retinal vein occlusion, in a patient in need thereof, by applying ultrasound energy to the eye using the ultrasound probe or system disclosed herein in order to identify an area of blockage within the vessels of the eye.

In one embodiment, the ultrasound probe can be used to accurately measure intraocular lens calculations and to accurately measure intraocular structures such as the retina as well as pathological structures such as tumors.

In a particular embodiment, the ultrasound probe can be used to activate or create inertial or unstable cavitation in a microbubble contrast agent and, optionally, to allow simultaneous viewing of the effects of such sonolysis on retinal blood flow and retinal structures. In one example, ocular blood flow may be monitored and adverse effects, such as bleeding, may be identified using the methods described herein.

In a particular embodiment, the ultrasound probe can be used to activate the microbubbles (which may be located within the eye, including within the vasculature of the eye or within the eye tissue including the lens material or trabecular meshwork) in order to create inertial or unstable cavitation in a microbubble containing drug or dye label and optionally, allow simultaneous viewing of the effects of such sonolysis on drug and/or dye release in the eye. In one embodiment, the microbubbles may be coated or filled with a therapeutic agent, for example, a drug, with ultrasonic shock waves activating the coating or causing mini explosions to release the therapeutic. Loading the microbubbles with a therapeutic agent, visualizing their presence at the diseased site using the ultrasound and optical diagnostic mode, and then activating the microbubbles to release their contents at the targeted lesion/region can be a powerful and effective way to reverse occlusion without harming other areas of the eye or body.

In another particular embodiment, the ultrasound probe can be used to create inertial or unstable cavitation in a microbubble contrast agent and optionally, allow simultaneous viewing of the effects of such sonolysis on phacomemulsification (ultrasound assisted breaking of human crystalline lens).

In another particular embodiment, the ultrasound probe can be used to create inertial or unstable cavitation in a microbubble contrast/dye agent (for example, protoporphyrin) and optionally, allow simultaneous application of laser to excite the dye.

The exemplary methods and acts described in the embodiments presented previously are illustrative, and, in alternative embodiments, certain acts can be performed in a different order, in parallel with one another, omitted entirely, and/or combined between different exemplary embodiments, and/or certain additional acts can be performed, without departing from the scope and spirit of the invention. Accordingly, such alternative embodiments are included in the inventions described herein.

Although specific embodiments have been described above in detail, the description is merely for purposes of illustration. It should be appreciated, therefore, that many aspects described above are not intended as required or essential elements unless explicitly stated otherwise. Modifications of, and equivalent acts corresponding to, the disclosed aspects of the exemplary embodiments, in addition to those described above, can be made by a person of ordinary skill in the art, having the benefit of the present disclosure, without departing from the spirit and scope of the invention defined in the following claims, the scope of which is to be accorded the broadest interpretation so as to encompass such modifications and equivalent structures.

What is claimed is:

1. An ocular ultrasound probe comprising:
   a housing with an outer ring, and
   an ultrasound transducer element disposed within the housing in a torus-shaped probe head,
   wherein the torus-shaped probe head is contoured similarly to the cornea of an eye and is configured for placement, during operation of the ultrasound probe, in contact with and onto the eye or an eyelid at a location designated for placement of a contact lens on the eye such that an open center portion of the torus-shaped probe head extends over a crystalline lens of the eye and the torus-shaped probe head encompasses the crystalline lens to deliver ultrasound energy to a target site in the eye around the crystalline lens while avoiding delivery of said energy to the crystalline lens,
   wherein the outer ring is dimensioned to retain and secure the ultrasound probe, which has been disposed in said contact with and onto the eye or the eyelid to hold the ultrasound probe in place; and
   wherein said ultrasound transducer element is configured to deliver ultrasound energy having a frequency lower than 10 MHz to the target site in the eye in order to initiate cavitation of microbubbles that have been delivered to an occluded retinal vein of the eye when said ultrasound probe has been disposed at said location and retained and secured with the use of the outer ring at the eyelid.

2. The ocular ultrasound probe of claim 1, wherein the ultrasound energy has a frequency of less than 5 MHz.

3. The ocular ultrasound probe of claim 1, wherein the ultrasound probe is an extraocular probe.

4. The ocular ultrasound probe of claim 1, wherein the ultrasound probe is an intraocular probe.

5. The ocular ultrasound probe of claim 1, further comprising a sensor configured to detect a change in an electrical field at an outer surface of the housing and to generate a signal indicating when the housing of the ultrasound probe is in contact with the eyelid or a surface of the eye at said location.

6. The ocular ultrasound probe of claim 1, further comprising an optical imaging component configured for viewing the target site through said optical imaging component simultaneously with delivering the ultrasound energy to the target site from the transducer during operation of the ultrasound probe.

7. The ocular ultrasound probe of claim 1, further comprising a laser illumination source.

8. A method for treating a disease or disorder of ocular blood flow, the method comprising:
   a) supplying microbubbles to a blockage within a retinal vessel, said supplying including supplying the microbubbles to an occluded retinal vein containing the blockage, and b) using an ultrasound probe that includes a housing with an outer ring and an ultrasound transducer element disposed within the housing in a torus-shaped probe head that is contoured similarly to the cornea of an eye and is configured for placement in contact with and onto the eye or an eyelid at a location designated for placement of a contact lens onto the eye to establish contact between the torus-shaped probe head and the eyelid or the eye at said location such that an open center portion of the torus-shaped probe head extends over a crystalline lens of the eye and the torus-shaped probe head encompasses the crystalline lens, and to secure the ultrasound probe at the eyelid with the use of said outer ring; and c) delivering ultrasound energy having a frequency lower than 10 MHz to a target site including a retina of the eye from the ultrasound transducer element in order to initiate cavitation of the microbubbles while avoiding delivery of said ultrasound energy to the crystalline lens of the eye.

9. The method of claim 8, wherein the ultrasound probe includes an optical imaging component in said housing and further comprising viewing said target site through the optical imaging component simultaneously with the delivering of said ultrasound energy.

10. The method of claim 8, wherein said delivering includes delivering said ultrasound energy to reduce or eliminate retinal vein occlusion.

11. The method of claim 8, wherein said supplying the microbubbles includes supplying the microbubbles with diameters in a range from 1 micron to 10 microns.

12. The method of claim 8, comprising moving the ultrasound probe along the eyelid or the eye.

13. The method of claim 8, wherein said supplying the microbubbles comprises supplying the microbubbles that include a therapeutic agent on surfaces or within interiors of the microbubbles.

14. The method of claim 13, wherein the delivering of said ultrasound energy to the target site includes rupturing the microbubbles to release the therapeutic agent.

* * * * *